United States Patent [19]

Briggs

[11] Patent Number: 4,540,831
[45] Date of Patent: Sep. 10, 1985

[54] MIXED-PHASE HYDROCARBON CONVERSION PROCESS EMPLOYING TOTAL OVERHEAD CONDENSER

[75] Inventor: Bruce A. Briggs, Buffalo Grove, Ill.

[73] Assignee: UOP Inc., Des Plaines, Ill.

[21] Appl. No.: 611,459

[22] Filed: May 17, 1984

[51] Int. Cl.³ .................. C07C 41/06; C07C 43/04; C07C 29/04; C07C 39/06

[52] U.S. Cl. .................. 568/697; 568/672; 568/785; 568/899; 585/375; 585/446

[58] Field of Search .............. 568/697; 260/698, 700

[56] References Cited

U.S. PATENT DOCUMENTS

| | | | |
|---|---|---|---|
| 2,373,501 | 4/1945 | Peterson | 568/894 |
| 3,824,289 | 7/1974 | Liggett | 260/700 |
| 3,989,762 | 11/1976 | Ester | 260/641 |
| 4,087,471 | 5/1978 | Bowman et al. | 568/899 |
| 4,232,177 | 11/1980 | Smith, Jr. | 585/324 |
| 4,281,206 | 7/1981 | Brandes et al. | 568/396 |
| 4,475,005 | 10/1984 | Paret | 568/697 |

OTHER PUBLICATIONS

Hamilton et al., "Organic Synthesis", vol. 29, (1949), pp. 11-14 and 89-91.
Oil and Gas Journal, 01-01-79, pp. 76-77, "Methyl Tertiary Butyl Ether Process Can Help Separate All C4 Fractions".
Hydrocarbon Processing, Nov. '72, pp. 113-116, "Use Cation Catalyst for IPA" by W. Neier and J. Woeliner.

*Primary Examiner*—J. E. Evans
*Attorney, Agent, or Firm*—Thomas K. McBride; William H. Page, II; John F. Spears, Jr.

[57] ABSTRACT

A process is disclosed for performing an exothermic reaction such as the etherification of isobutylene with methanol. The feed is charged to a vertical reaction zone containing a solid catalyst. Heat released by the exothermic reaction partially vaporizes the reactants, with the vapors traveling upward to a condensing zone. All of the condensable vapors entering the condensing zone are condensed and returned downward to the catalyst bed. A single effluent stream made up of the product, excess reactants and any unreactive compounds present in the feed streams is removed from the bottom of the reaction zone. This total reflux reaction zone allows temperature control within a catalyst bed without the use of indirect heat exchangers located within the reaction zone.

10 Claims, 1 Drawing Figure

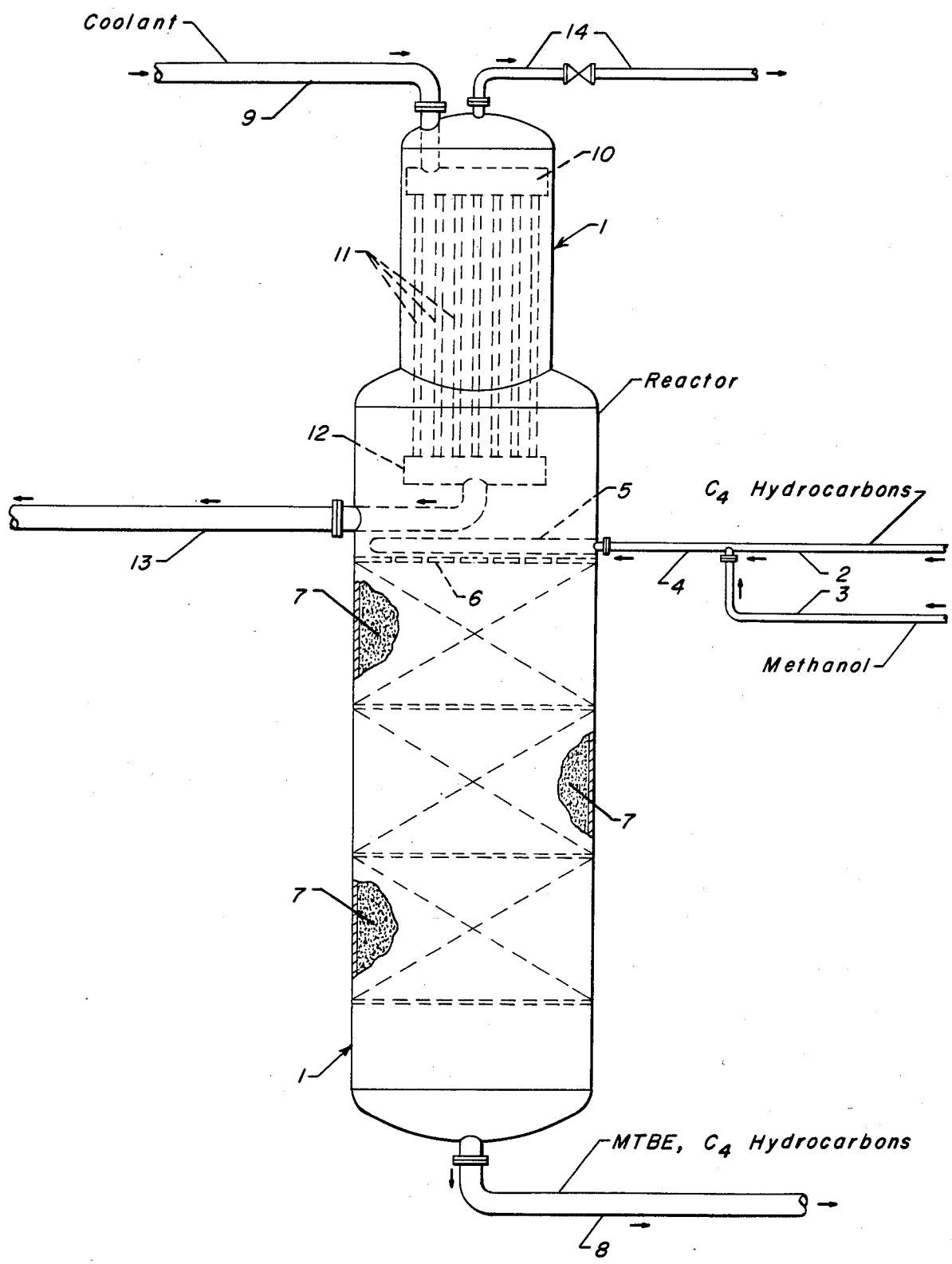

MIXED-PHASE HYDROCARBON CONVERSION PROCESS EMPLOYING TOTAL OVERHEAD CONDENSER

FIELD OF THE INVENTION

The invention relates to a process for performing exothermic chemical reactions which consume at least one volatile reactant. The invention specifically relates to a process for performing exothermic hydrocarbon conversion reactions which may be performed under conditions at which heat released by the reaction can vaporize one of the reactants. The invention also relates to the design of reactors used to perform exothermic reactions and to the means used to remove heat from a reaction zone in order to avoid excessive operating temperatures. Specific reactions which may be performed in the subject process include etherification reactions between olefins and alcohols and alkylation reactions. The invention therefore also relates to the production of ethers such as the production of methyl tertiary butyl ether by the reaction of methanol and isobutylene.

INFORMATION DISCLOSURE

It is well known to those skilled in the art that it is often desirable or necessary to remove the heat of reaction from a reaction zone. This may be for one or more reasons including a desire to achieve better selectivity or to increase catalyst life. It is known that excessive heat can be removed from a reaction zone in a number of different ways. For instance, in U.S. Pat. No. 4,087,471 (Bowman) a sizeable recycle stream is passed through the reactor, with the recycle stream being cooled outside of the reactor. A more traditional method of heat removal employs indirect heat exchangers placed with the reaction zone. This is shown in U.S. Pat. No. 3,989,762 (Ester) and in the article at page 76 of the Jan. 1, 1979 edition of *The Oil and Gas Journal*. The former reference describes a process for production of alcohols by the direct hydration of olefins. The latter reference is also pertinent for its teaching in regard to the production of methyl tertiary butyl ether.

U.S. Pat. No. 4,281,206 (Brandes, et al) describes a reactor system referred to as a trickle-type reactor. In this type of reactor a mixture of a vaporous reactant and a liquid reactant is charged to the top of a fixed bed of catalyst. The mixed-phase reactants pass downward and exit the bottom of the reactor together with the reaction products. The use of this reactor for the exothermic reactions including the direct hydration of olefins and the production of ketones using a strongly acid cation exchange resin is disclosed in this reference. It is known in the art that the mixed-phase effluent of this type of reactor can be passed into a high pressure separator for separation into liquid and vapor streams. This is shown in FIG. 2 of the article starting at page 113 of the November 1972 edition of *Hydrocarbon Processing*.

U.S. Pat. No. 4,232,177 (Smith) is pertinent for its description of catalytic distillation reactor systems. In this type of system a fractional distillation is performed concurrently with the reaction. The reaction product is a less volatile compound removed in the net bottoms stream of the fractionation column. This product is formed during contact with solid resin catalyst present in the column as packing. Volatile components of the feed stream which are not consumed in the reaction are removed overhead, with an overhead condensing system being employed to generate reflux. One of the advantages ascribed to this process in column six of the reference is that since the $C_4$ components are boiling at the chosen operating conditions, the temperature of the reaction zone is controllable. Heat released by the reaction generates more vapor. The rate of reaction and product distribution can therefore be controlled by regulating the pressure of the reaction-fractionation vessel.

BRIEF SUMMARY OF THE INVENTION

The invention is a process for performing exothermic chemical reactions which provides effective temperature control of the reactants in a simple low-cost system. The reactor system does not require multitube reactors or interstage coolers to remove the heat of reaction. The process is also expected to reduce olefin oligomerization in olefin alkylation and etherification processes. In the subject process heat is removed by vaporization, with all of the thus vaporized reactants and inerts being condensed and returned to the reaction site. This total reflux of volatile compounds requires all unreacted compounds to eventually exit from the bottom of the reaction zone. Volatile compounds are therefore carried downward through the entire reaction zone and are available for temperature control at all points in the catalyst bed. Other advantages of the subject process are set out below.

A broad embodiment of the invention may be characterized as a hydrocarbon conversion process which comprises the steps of passing a first chemical compound and a second chemical compound into a reaction zone maintained at reaction-promoting conditions and containing a solid catalyst which promotes an exothermic reaction between the first and second chemical compounds to form a third chemical compound, with the third compound being less volatile than the first and second compounds, and with a vapor phase being formed within the reaction zone at least in part by the vaporization of the first and/or second compounds from heat released in said exothermic reaction; totally condensing said vapor phase in an upper portion of the reaction zone by indirect heat exchange to form condensate liquid which descends within the reaction zone; removing a liquid phase effluent stream from a bottom portion of the reaction zone, with the effluent stream comprising the third compound and substantially all of the first and second compound which is not consumed in said reaction; and recovering the third compound from the effluent stream.

BRIEF DESCRIPTION OF THE DRAWING

The drawing illustrates one embodiment of the invention in which a specific apparatus is used to perform an etherification reaction to produce methyl tertiary butyl ether (MTBE). Other apparatus and processes set out below illustrate that the invention is not limited to this specific embodiment. Referring now to the drawing, a first feed stream comprising an admixture of $C_4$ hydrocarbons including butanes and isobutylene from line 2 is admixed with a stream of substantially anhydrous methanol from line 3. The resulting feed admixture is passed through line 4 into a horizontal distributor 5. The entering liquids are further distributed by a perforated plate 6 located above the uppermost of three catalyst beds 7. These catalyst beds occupy substantially all of the cross-sectional area of the reaction vessel 1.

The reaction vessel is maintained at a pressure such that heat released by the exothermic etherification reaction causes the vaporization of $C_4$ hydrocarbons. The hydrocarbon vapors travel upward within the catalyst beds and void volumes of the reaction zone until they contact the indirect heat exchange tubes 11. These tubes contain coolant supplied through line 9 and distributed in the manifold 10. The coolant is collected in the manifold 12 and withdrawn through line 13. The outer surface of the tubes is maintained at a sufficiently low temperature that the $C_4$ hydrocarbons in contact with the tubes are condensed. The resultant condensate falls downward and returns to the catalyst beds. The MTBE formed within the catalyst bed and the remaining $C_4$ hydrocarbons descend through the catalyst bed and are removed as a single combined effluent stream carried by line 8. Any very volatile material such as nitrogen or methane which accumulates in the upper portion of the vessel is removed as required through line 14.

DETAILED DESCRIPTION

The subject invention provides a process and apparatus for practicing highly exothermic chemical reaction. It is an objective of the invention to provide highly dependable temperature control of the reaction zone of such an exothermic process. It is also an objective of the invention to eliminate the need for complicated and expensive indirect heat exchange systems in catalyst beds used for exothermic reactions. It is a further objective of the invention to provide a reaction zone which minimizes by-product formation. It is a specific objective of the invention to provide an improved reaction system for alkylation and etherification reactions in which isobutylene is consumed.

The apparatus required to perform the subject process comprises two basic components. These two components are a vertical process vessel containing solid catalyst and an overhead condenser. The process vessel is preferably a cylindrical metal pressure vessel similar to that commonly used in other petroleum refining processes. This vessel contains a solid catalyst which promotes the desired reaction. Preferably this catalyst is divided between a number of separate beds located at different elevations within the column. These beds are preferably segregated by horizontal means which restrict the movement of catalyst particles but allow the free vertical transfer of both vapor and liquid. These horizontal devices are preferably perforated in a manner such that they also act as liquid redistribution means to prevent the descending liquid from "channeling" through portions of the catalyst containing region of the apparatus. In the preferred embodiments of the invention, these horizontal liquid redistribution means support only the catalyst which is located immediately above each means. This support function is important when a resin type catalyst is employed as it prevents excess compaction of the resin. A void space may be provided under each redistribution support means to allow for catalyst expansion. These devices are preferably suspended from the inner surface of the vessel wall. From 2 to 6 of the devices are preferred. This arrangement does not provide separate fluid flow paths which do not contain catalyst such as the more complicated system described in the previously cited U.S. Pat. No. 4,232,177. The catalyst may fill substantially all of the reaction vessel or just a lower portion of it when an internal condenser is employed.

The feed streams are preferably admixed outside of the reaction vessel and then distributed across the upper surface of the upper catalyst bed. The feed stream admixture can also be charged to the reaction vessel at two or more points such as above and just below the uppermost catalyst bed. The feed streams are preferably charged to the reaction zone at a temperature just slightly below the desired reaction temperature.

The subject invention employs a condenser or condensing zone which is capable of condensing all of the vapors produced in the reaction vessel. This condenser may be located within the reaction vessel as shown in the drawing or may be located externally. If the condenser is located externally to the reaction zone, the entire condenser system will preferably resemble the overhead system of a fractionation column. Vapors are then removed from the top of the reaction vessel and passed through the condenser. The effluent of the condenser, which is substantially all liquid, is then preferably collected in an overhead receiving vessel prior to being returned to the reaction zone. This collection is not necessary but allows the rate of condensation to be more easily monitored. Any uncondensed vapor is vented from the receiving vessel. The liquid formed by external condensation may be returned to the reaction vessel separately or in admixture with the feed streams. In an alternative arrangement portions of the condensate are returned at several different points within the catalyst-containing sections of the reaction zone to further promote temperature control. The mechanical structure of the condenser does not govern the operation of the process. The condenser may be a plate or a horizontal tubular indirect heat exchanger. The preferred cooling media is water although air, commercial heat exchange fluids, etc. can be employed.

Regardless of the configuration of the condensing means, the function remains the same. This function is the condensation of vapors produced in the reaction at a rate equal to their rate of production. All of the resulting condensate liquid is then preferably returned to the catalyst-containing zone of the reaction vessel, thus resulting in a total reflux operation. In some rare instances it may be desired to remove some of the condensate to withdraw relatively volatile but still condensable compounds which would not exit in the liquid withdrawn from the bottom of the reaction zone. This could be, for example, water which collects in a receiver boot in a process consuming $C_6$-plus hydrocarbons. The only compounds always removed from the upper portion of the reaction or condensing systems are compounds which are not condensed by the condensing system. These compounds will basically be various highly volatile impurities which may be dissolved in the feed streams such as hydrogen, nitrogen, methane, carbon dioxide, etc. These compounds are often referred to in the art as "noncondensables". This is due to the fact that they do not condense at commercially feasible operating conditions such as a temperature of 50° F. (10° C.). As used here the term total condensation refers to the condensation of all compounds other than these noncondensables.

The accumulation of noncondensable gases in the condensing system will hinder the operation of the condensing system. These gases will therefore be drawn off. Vapors may also be removed from the top of the reaction zone for the purpose of quick response pressure control such as for emergency temperature control. However, it is greatly preferred to only vent sufficient gases to remove noncondensables, with pressure control being achieved by controlling the condenser temperature. It is preferred that discharged vapors are first passed through the condensing means. It is further preferred that any gases vented in this manner are also passed through a separate vent gas condenser, not shown in the drawing, in order to recover any condensable reactants, which are then returned to the reaction zone. Controlling the pressure within the reaction zone is important since the pressure sets the boiling point of the liquid-phase reactant mixture. The operating temperature of the catalyst beds can therefore be adjusted by increasing or decreasing the system pressure. The subject process therefore provides a convenient and simple method of controlling one of the most important operating variables in most reactions. The invention also eliminates the need for indirect heat exchangers in the catalyst bed.

Another advantage of the subject process resides in the larger vapor and liquid flow rates through the catalyst beds compared to a reaction system which is cooled by indirect heat exchange. A reactor which is cooled by heat exchangers located within the catalyst will have less vapor flowing through the catalyst bed. There will also be less liquid flowing through the catalyst bed in a heat exchange cooled system since there is no net condensate flow. Further, the countercurrent vapor-liquid flow of the subject reaction system is not found in the heat exchange cooled systems. The subject process therefore provides increased fluid flow and better mixing in the catalyst beds. This results in smaller temperature and reactant concentration profiles and improved operations.

A further advantage provided by the subject reaction system is improved selectivity over comparable prior art systems which operate with totally liquid phase reactants. Examples of this are found in some processes for the alkylation of aromatic hydrocarbons and some etherification processes. This advantage is provided when a more volatile reactant has a tendency to react with itself to form by-products such as oligomers or to react with the less volatile reactant to a greater extent than desired. An example of the latter situation is the production of bi- and trialkyl aromatics in a process intended to produce monoalkyl aromatics. By maintaining a vapor-phase in the reaction zone, the mole ratio in the liquid phase of the less volatile reactant to the more volatile reactant is increased. Since the liquid phase is in contact with the catalyst, the desired reaction is promoted. For example, it is believed that the tendency of volatile components present in the vapor phase, such as isobutylene, to react to form oligomers will be reduced since the vapor is separated from the catalyst by the liquid coating the catalyst. The volatile reactants must diffuse through the liquid to reach the catalytic sites.

A preferred embodiment of the subject invention may be characterized as a hydrocarbon conversion process which comprises the steps of passing a first chemical compound and a second chemical compound into a vertical unitary reaction zone maintained at reaction-promoting conditions and containing a bed of a solid catalyst which promotes an exothermic reaction between the first and the second compounds to form a third chemical compound, with the third compound being less volatile than the first and second compounds, and with a vapor phase being formed within the reaction zone at least in part by the vaporization of the first and/or second compounds by heat released in said exothermic reaction; passing a vapor phase stream comprising the first compound into a condensing zone located above the bed of catalyst, and forming condensate by condensing essentially all of the vapor phase stream; passing the condensate downward into the bed of catalyst; withdrawing a liquid phase effluent stream which comprises the first, second and third chemical compounds from a bottom portion of the reaction zone, with the effluent stream comprising substantially all of the first and second compound which is not consumed in said reaction; and recovering the third compound from the effluent stream. It is to be noted that the effluent stream removed from the bottom of the reaction zone is a liquid phase stream. Therefore substantially all of the reactants, products and diluent compounds are removed as liquids in the bottom stream, with the only exception being the limited amount of vapor removed overhead to remove noncondensables or control reactor pressure as described above.

The subject process is highly useful when employed as an alkylation process. This reaction comprises the addition of an olefin or olefin-acting compound to an alkylatable compound. The olefin is preferably a $C_3$ to $C_5$ monoolefin. The alkylatable compound can be a cyclic hydrocarbon such as cyclohexane or an aliphatic saturated $C_6$ to $C_{15}$ hydrocarbon, but is preferably an aromatic hydrocarbon. The preferred aromatic hydrocarbons are those containing a single benzene ring such as benzene, toluene, xylene, phenols and cresols. A particularly preferred reaction is the dialkylation of p-cresol with isobutylene to yield 2,6-di-t-butyl-p-cresol (BHT). This may be performed using cationic sulfonic acid-type resin catalysts. Preferred operating conditions for this reaction include a temperature of about 85°–100° C. at a pressure greater than 100 psig. A general range of alkylation conditions which may be employed with other reactants include a temperature of from about 35° to about 145° C. and a pressure of from about 10 to about 350 psig. A wide variety of catalysts may be employed including solid phosphoric acid catalysts such as described in U.S. Pat. Nos. 3,132,109; 3,293,315 and 3,402,130. It is also known that hydrocarbons can be alkylated using a catalyst which comprises a crystalline aluminosilicate. These catalysts can contain various metals such as iron, cobalt, rhodium or osmium to support the catalytic function. Exemplary zeolite-containing catalysts are described in U.S. Pat. Nos. 2,904,607; 3,751,506; 4,379,761; 4,387,259; 4,387,260 and 4,394,300. The products of these alkylation reactions may be branched chain aliphatics, mono- or dialkylated aromatics, etc.

As previously mentioned, the subject reaction system is highly suited to the performance of etherification reactions in which an olefinic hydrocarbon is reacted with an alcohol. The preferred alcohol is methanol. The next preferred alcohol after methanol is ethanol, but other alcohols such as propanols, ethylene glycol or propylene glycol can also be consumed in the process. The subject process can therefore be applied to the production of ethers other than MTBE including methyl tertiary amyl ether, ethyl tertiary amyl ether, and ethyl tertiary butyl ether. The olefinic hydrocarbon preferably has less than six carbon atoms per molecule, with isoolefins being especially preferred. The olefin-containing feed stream should contain over 30 mole percent of the desired feed olefin. A one carbon number mixture of hydrocarbons recovered from the effluent of a fluidized catalytic cracking unit is a suitable olefin feed stream for MTBE production.

The reaction conditions maintained in the catalyst-containing portions of the reaction zone during etherification will depend on the reactants and the catalyst. As an example, a broad range of etherification conditions suitable for the production of MTBE includes a superatmospheric pressure sufficient to maintain some liquid phase hydrocarbons, generally below about 200 psig and a temperature between about 30° and 100° C. A preferred temperature range is from 50° to 100° C. The mole ratio of feed alcohol to isoolefin should normally be maintained in the broad range of from 1:1 to 3:1. Good results are achieved if the ratio of methanol to isobutene is between 1.1:1 and 1.5:1. A wide range of materials is known to be effective as etherification catalysts including phosphoric acid on kieselguhr, phosphorus-modified zeolites and various sulfonated resins. The use of a sulfonated solid resin etherification catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. No. 4,270,929.

When the subject process is used for the direct hydration of olefins, the catalyst-containing portion(s) of the reaction zone should contain at least a molar excess of water over that which is stoichiometrically required for the hydration reaction. The water concentration within the reaction zone is an important variable in the process. It is preferred that the molar ratio of water to feed olefinic hydrocarbon is between about 0.5:1 and 20:1. More preferably, this ratio is between about 1:1 and about 10:1. Each mole of the olefinic hydrocarbon charged to the reaction zone therefore requires the presence of from about 1 to about 10 moles of water. Most of this water is provided by a recycle stream from downstream product recovery operations. Only a small proportion of the water is actually consumed in the hydration reaction. The product alcohol is withdrawn from the reaction vessel as a part of a relatively dilute aqueous alcohol solution.

The hydration conditions which are suitable for the subject process include a pressure of from about 50 to about 250 psig. Preferably, the reaction zone is maintained at a pressure of from about 75 to about 100 psig. The reaction zone is preferably operated at a temperature between about 40° and about 120° C. A preferred operating inlet temperature is between about 135° and about 160° C. These conditions are those which are preferred for the conversion of isobutylene to tertiary butyl alcohol. The preferred conditions will vary with different feed olefins and with catalysts other than the preferred resin-type catalyst. The rate of water flow through the catalyst bed should be between about 1 and about 40 and preferably about 5 and about 25 moles of water per cm$^2$ of cross-sectional area per hour.

As the subject invention basically relates to a method of contacting the reactants and catalyst, the hydration embodiment is also not limited to any particular hydration catalyst. The subject process may therefore be employed utilizing the presently preferred catalyst or those which are the result of the continuing research effort in this area. The presently preferred hydration catalysts are ion-exchange catalysts or resins. The preferred resins comprise a copolymer of styrene and divinylbenzene. It is further preferred that these copolymer resins are treated with a sulfur-containing acid to yield a highly acidic sulfonic acid-containing resin. In general, the catalyst should contain from about 0.2 to 1 sulfonic acid group per aromatic ring present in the resin. These catalysts may be further modified as by chlorination, fluorination, etc., which has been shown to yield improved high temperature stability. A particularly preferred resin of this nature is described in U.S. Pat. No. 4,340,769. Suitable catalysts are available from commercial sources.

I claim as my invention:

1. An exothermic etherification process for the continuous reaction of an olefinic hydrocarbon having less than six carbon atoms per molecule with an alcohol which comprises the steps of:
   (a) passing said olefinic hydrocarbon and said alcohol into a reaction zone maintained at reaction-promoting conditions and containing a solid etherification catalyst which promotes said exothermic etherification between said olefinic hydrocarbon and said alcohol to form a corresponding ether compound which is less volatile than said alcohol and said olefinic hydrocarbon, and with a vapor phase being forward within the reaction zone at least in part by the vaporization of said alcohol, olefinic hydrocarbon or both, said alcohol and olefinic hydrocarbon vaporized as a result of heat released in said exothermic reaction;
   (b) condensing substantially all of the condensible vapor in said vapor phase in an upper portion of said reaction zone by indirect heat exchange with a fluid of lower temperature than said vapor phase to form a condensate liquid phase containing substantially all of said condensibles present in the vapor phase including both reactants comprising said olefinic hydrocarbon and said alcohol in liquid phase;
   (c) passing downwardly through the reaction zone from a point elevated with respect to the etherification catalyst all of said condensate liquid phase including both said reactant within said reaction zone;
   (d) removing said formed ether compounds as a liquid phase effluent stream from a bottom portion of said reaction zone in accompaniment with substantially all of said alcohol and olefinic hydrocarbon added to said reaction zone in step (a) and not consumed in said etherification reaction zone; and
   (e) recovering said ether compound from said liquid phase effluent stream.

2. The process of claim 1 further characterized in that the olefinic hydrocarbon is isobutylene.

3. The process of claim 2 further characterized in that the etherification catalyst comprises an acidic resin.

4. The process of claim 2 further characterized in that isobutylene is charged to the reaction zone in admixture with at least one other C$_4$ hydrocarbon, and in that said other C$_4$ hydrocarbon is removed from the reaction zone as part of the effluent stream.

5. An exothermic etherification process for the continuous reaction of olefinic hydrocarbons having four carbon atoms per molecule with an alcohol, which comprises the steps of:
   (a) passing said olefinic hydrocarbon and said alcohol into a reaction zone maintained at reaction-promoting conditions and containing a bed of solid etherification catalyst which promotes said exothermic etherification between said olefinic hydrocarbon and said alcohol to form a corresponding ether compound which is less volatile than said alcohol and said olefinic hydrocarbon, and with a vapor being formed within said reaction zone at least in part by the vaporization of said olefinic hydrocarbon and said alcohol by heat released in said exothermic reaction;

(b) passing said vapor phase containing both alcohol and olefinic compound into a condensing zone located above the bed of said etherification catalyst to form a condensate stream by condensing essentially all of said condensible compounds, including said alcohol and olefinic hydrocarbon, present in said vapor phase stream;

(c) passing all of said condensate including both of said reactants, downward into said bed of solid etherification catalyst from a position elevated with respect to said bed of etherification catalyst;

(d) withdrawing a liquid phase effluent stream which comprises said ether compound in accompaniment with all of said alcohol and olefinic hydrocarbon not consumed within said reaction zone from a bottom portion of said reaction zone; and (e) recovering said ether product from said bottoms effluent stream.

6. The process of claim 5 further characterized in that the $C_4$ olefinic hydrocarbon is isobutylene.

7. The process of claim 6 further characterized in that isobutylene is charged to the reaction zone in admixture with at least one other $C_4$ hydrocarbon, which is not significantly consumed in said reaction, and in that substantially all of the $C_4$ hydrocarbons other than isobutylene which enter the reaction zone are withdrawn from the reaction zone as a portion of the effluent stream in step (d).

8. The process of claim 5 further characterized in that the alcohol is methanol.

9. The process of claim 5 further characterized in that the condensing zone is not located in the same process vessel as the bed of solid catalyst.

10. The process of claim 5 further characterized in that the solid etherification catalyst comprises an acidic ion-exchange resin.

* * * * *